United States Patent [19]

Kunz et al.

[11] Patent Number: 5,302,607
[45] Date of Patent: Apr. 12, 1994

[54] COMPOSITIONS FOR PROTECTING PLANTS AGAINST DISEASE

[75] Inventors: Walter Kunz, Oberwil; Rolf Schurter, Binningen, both of Switzerland

[73] Assignee: Ciba-Geigy Corporation, Ardsley, N.Y.

[21] Appl. No.: 58,838

[22] Filed: May 6, 1993

Related U.S. Application Data

[63] Continuation of Ser. No. 905,064, Jun. 24, 1992, abandoned, which is a continuation of Ser. No. 737,826, Jul. 29, 1991, abandoned, which is a continuation of Ser. No. 481,423, Feb. 16, 1990, abandoned.

[30] Foreign Application Priority Data

Feb. 21, 1989 [CH] Switzerland .......................... 615/89

[51] Int. Cl.$^5$ .................... C07D 285/14; A01N 43/82
[52] U.S. Cl. .................... 514/361; 548/110; 548/126
[58] Field of Search .................... 548/110; 514/361

[56] References Cited

U.S. PATENT DOCUMENTS

| | | | |
|---|---|---|---|
| 4,931,581 | 6/1990 | Schurter | 560/18 |
| 5,051,436 | 9/1991 | Kunz | 514/361 |
| 5,066,661 | 11/1991 | Kunz | 514/361 |

FOREIGN PATENT DOCUMENTS

| | | | |
|---|---|---|---|
| 347377 | 12/1989 | European Pat. Off. | 548/126 |
| 1176799 | 1/1970 | United Kingdom . | |

Primary Examiner—Robert Gerstl
Attorney, Agent, or Firm—Edward McC.Roberts; Kevin T. Mansfield

[57] ABSTRACT

Novel benzo-1,2,3-thiadiazole-7-carboxylic acid esters of formula

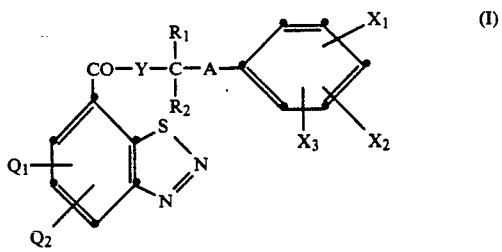

in which
Y is oxygen or sulfur;
$Q_1$ and $Q_2$ independently of one another are each hydrogen or halogen;
$R_1$ and $R_2$ independently of one another are each hydrogen or $C_1$-$C_4$alkyl; $X_1$ is hydrogen, halogen, $C_1$-$C_4$alkyl, trifluoromethyl, $C_1$-$C_3$alkyl, $C_1$-$C_2$alkoxy halosubstituted in the alkyl moiety, nitro, cyano, dimethylamino, phenyl, phenoxy, or phenyl or phenoxy each substituted by halogen and/or by $C_1$-$C_2$alkyl and/or by $C_1$-$C_2$alkoxy;
$X_2$ is hydrogen, halogen or methyl;
$X_3$ is hydrogen or halogen; and
A comprises the bridge member

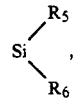

$R_5$ is $C_1$-$C_6$alkyl, $C_3$-$C_6$cycloalkyl, $C_1$-$C_6$alkoxy, phenyl, or phenyl substituted by halogen or methoxy;
$R_6$ is $C_1$-$C_6$alkyl or $C_1$-$C_6$alkoxy;

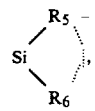

that together represents a saturated or unsaturated 3- to 7-membered heterocycle $W_3$ having a maximum of 2 oxygen or sulfur atoms as additional hetero atoms.

The novel active ingredients have plant-protecting properties and are suitable especially for the preventive protection of plants against attack by phytopathogenic microorganisms such as fungi, bacteria and viruses.

6 Claims, No Drawings

COMPOSITIONS FOR PROTECTING PLANTS AGAINST DISEASE

This application is a contination of application Ser. No. 07/905,064 filed Jun. 24, 1992, now abandoned, which is a contination of Ser. No. 07/737,826 filed Jul. 29, 1991, now abandoned, which is a continuation of Ser. No. 07/481,423 filed Feb. 16, 1990, now abandoned.

The present invention relates to novel benzo-1,2,3-thiadiazole-7-carboxylic acid esters of the following formula I. The invention relates also to the preparation of those substances and to compositions containing at least one of those compounds as active ingredient. The invention furthermore relates to the preparation of the said compositions and to the use of the active ingredients or compositions for protecting plants against attack by harmful microorganisms, for example plant-damaging fungi, bacteria and viruses.

The compounds of the invention correspond to the general formula I

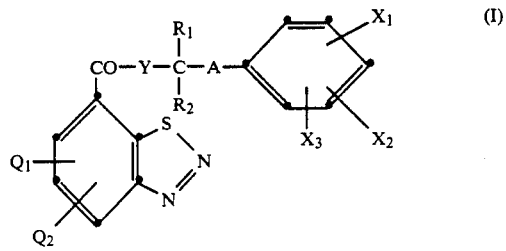

in which

Y is oxygen or sulfur;

$Q_1$ and $Q_2$ independently of one another are each hydrogen or halogen;

$R_1$ and $R_2$ independently of one another are each hydrogen or $C_1$–$C_4$alkyl;

$X_1$ is hydrogen, halogen, $C_1$–$C_4$alkyl, trifluoromethyl, $C_1$–$C_3$alkyl, $C_1$–$C_2$alkoxy halo-substituted in the alkyl moiety, nitro, cyano, dimethylamino, phenyl, phenoxy, or phenyl or phenoxy each substituted by halogen and/or by $C_1$–$C_2$alkyl and/or by $C_1$–$C_2$alkoxy;

$X_2$ is hydrogen, halogen or methyl;

$X_3$ is hydrogen or halogen; and

A comprises the bridge members

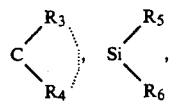

carbonyl, ethenylene and ethynylene, wherein $R_3$ is $C_1$–$C_6$alkyl, $C_3$–$C_6$alkenyl, hydroxy, $C_1$–$C_6$alkoxy, O—C(O)—$C_1$–$C_4$alkyl, carboxy, $COOC_1$–$C_4$alkyl, cyano or hydrogen, with the proviso that if $R_3$ is hydrogen $R_1$, $R_2$ or $R_4$ is not simultaneously hydrogen;

$R_4$ is $C_1$–$C_6$alkyl, $C_1$–$C_6$alkoxy or hydrogen, with the proviso that if $R_4$ is hydrogen $R_1$, $R_2$ or $R_3$ is not simultaneously hydrogen;

$R_5$ is $C_1$–$C_6$alkyl, $C_3$–$C_6$cycloalkyl, $C_1$–$C_6$alkoxy, phenyl, or phenyl substituted by halogen or by methoxy;

$R_6$ is $C_1$–$C_6$alkyl or $C_1$–$C_6$alkoxy;

or alternatively A represents the bridge member

that together also represents a saturated or unsaturated 3- to 7-membered carbocycle $W_1$ or a saturated or unsaturated 5-to 7-membered heterocycle $W_2$ having 1 or 2 hetero atoms that are either oxygen, sulfur or nitrogen; or the bridge member

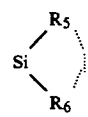

that together represents a saturated or unsaturated 3- to 7-membered heterocycle $W_3$ having a maximum of 2 oxygen or sulfur atoms as additional hetero atoms.

As carbocyclic rings $W_1$, the following, for example, may be mentioned: cyclopropyl, cyclobutyl, cyclopentyl, cyclohexyl and cycloheptyl or cycloheptenyl, preferably cyclopropyl, cyclopentyl and cyclohexyl. Suitable heterocycles $W_2$ are, for example, 1,3-dioxolan-2-yl, 1,3-dioxolan-4-on-5-yl, tetrahydrofuran-2-yl, tetrahydrofuran-2-on-3-yl, 1,3-dithiolan-2-yl, 1,3-dioxan-2-yl, tetrahydropyran-2-yl, tetrahydro-1,3-oxazin-2-yl, oxazolidin-2-yl, 1,3-dithian-2-yl and 1,3-dioxacyclohepten-(4)-2-yl.

Suitable heterocycles $W_3$ are, for example, 1-sila-2,6-dioxacyclohexane, 1-sila-2,5-dioxacyclopentane, 1-sila-2,7-dioxacycloheptane, 1-sila-2,5-dioxacyclohexane, 1-sila-2-oxocyclopentane, 1-sila-2-oxocyclohexane, 1-sila-2,6-dithiacyclohexane, sila-cyclopentane, sila-cyclohexane, sila-cycloheptane and 1-sila-cyclohep-tene-4.

The mentioned cyclic radicals $W_1$, $W_2$ and $W_3$ may be unsubstituted or carry from 1 to 3 substituents V.

V may be $C_1$–$C_6$alkyl, $C_1$–$C_6$haloalkyl having up to 5 halogen atoms, preferably fluorine atoms, $C_1$–$C_3$alkoxy, halo-substituted $C_1$–$C_3$alkoxy, or $C_1$–$C_6$alkyl interrupted by O or S or substituted by phenyl or phenoxy.

Halogen is fluorine, chlorine, bromine or iodine, preferably fluorine and then, in order of preference, chlorine, bromine and iodine. From 1 to 3 halogen atoms may be present as substituents in individual radicals.

Alkyl on its own or as a component of another substituent is to be understood as meaning straight-chain or branched alkyl. Depending on the number of carbon atoms indicated it represents, for example, one of the following groups: methyl, ethyl or an isomer of propyl, butyl, pentyl or hexyl, such as, for example, isopropyl, isobutyl, tert.-butyl, sec.-butyl or isopentyl.

Alkenyl is, for example, propenyl-(1), allyl, butenyl-(1), butenyl-(2) or butenyl-(3) and alkynyl is, for example, propynyl-(2), butynyl-(1) or pentynyl-(4).

The compounds of formula I can be divided into the following groups on the basis of their particular plant-protecting properties:

1. Compounds of formula I in which

Y is oxygen or sulfur;

$Q_1$ and $Q_2$ independently of one another are each hydrogen or halogen;

$R_1$ and $R_2$ independently of one another are each hydrogen or $C_1$–$C_4$alkyl;

$X_1$ is hydrogen, halogen, $C_1$–$C_4$alkyl, trifluoromethyl, $C_1$–$C_3$alkyl, $C_1$–$C_2$alkoxy halo-substituted in the alkyl moiety, nitro, cyano, dimethylamino, phenyl, phenoxy, or phenyl or phenoxy each substituted by halogen and/or by $C_1$–$C_2$alkyl and/or by $C_1$–$C_2$alkoxy;

$X_2$ is hydrogen, halogen or methyl;
$X_3$ is hydrogen or halogen; and
A comprises the bridge members,

carbonyl, ethenylene and ethynylene wherein $R_3$ is $C_1$–$C_6$alkyl, $C_3$–$C_6$alkenyl, hydroxy, $C_1$–$C_6$alkoxy, O—C(O)—$C_1$–$C_4$alkyl, carboxy, COOC$_1$–$C_4$alkyl, cyano or hydrogen, with the proviso that if $R_3$ is hydrogen $R_1$, $R_2$ or $R_4$ is not simultaneously hydrogen;

$R_4$ is $C_1$–$C_6$alkyl, $C_1$–$C_6$alkoxy or hydrogen, with the proviso that if $R_4$ is hydrogen $R_1$, $R_2$ or $R_3$ is not simultaneously hydrogen; or alternatively A represents the bridge member

that together also represents a saturated or unsaturated 3- to 7-membered carbocycle $W_1$ or a saturated or unsaturated 5-to 7-membered heterocycle $W_2$ having 1 or 2 hetero atoms that are either oxygen, sulfur or nitrogen.

2. Compounds of formula I in which
Y is oxygen;
$Q_1$ and $Q_2$ independently of one another are each hydrogen, fluorine, chlorine or bromine;
$R_1$ and $R_2$ independently of one another are each hydrogen, methyl or ethyl;
$X_1$ is hydrogen, halogen, $C_1$–$C_4$alkyl, $C_1$–$C_3$alkoxy, phenyl, phenoxy, or phenyl or phenoxy each substituted by halogen or by $C_1$–$C_2$alkyl;
$X_2$ is hydrogen or halogen; $X_3$ is hydrogen;
A represents the bridge members,

ethenylene, ethynylene and carbonyl;
$R_3$ is $C_1$–$C_6$alkyl, $C_3$–$C_6$alkenyl, hydroxy, $C_1$–$C_6$alkoxy, cyano or COOC$_1$–$C_3$alkyl;
$R_4$ is hydrogen, methyl, ethyl, methoxy or ethoxy;
$W_1$ is cycloheptyl, cyclohexyl, cyclopentyl, cyclobutyl or cyclopropyl;
$W_2$ is 1,3-dioxolan-2-yl, 1,3-dioxan-2-yl, 1,3-dioxolan-4-on-5-yl, tetrahydrofuran-2-on-5-yl, 1,3-dithian-2-yl, tetrahydro-1,3-oxazin-2-yl or oxazolidin-2-yl.

3. Compounds of formula I in which
Y is oxygen;
$Q_1$ and $Q_2$ independently of one another are each hydrogen or fluorine;
$R_1$ and $R_2$ are hydrogen or methyl; $X_1$ is hydrogen, halogen, methyl, ethyl, methoxy, ethoxy, phenyl, phenoxy, or phenyl or phenoxy each substituted by fluorine, chlorine, methyl or by ethyl;

$X_2$ is hydrogen or halogen;
$X_3$ is hydrogen;
A represents the bridge members,

ethenylene and ethynylene;
$R_3$ is $C_2$–$C_4$alkyl, $C_3$–$C_6$alkenyl, hydroxy, O—$C_1$–$C_4$alkyl, cyano or COOC$_1$–$C_3$alkyl;
$R_4$ is hydrogen, methyl, ethyl, methoxy or ethoxy;
$W_1$ is cyclopentyl or cyclohexyl;
$W_2$ is 1,3-dioxolan-2-yl, 1,3-dioxan-2-yl, 1,3-dioxolan-4-on-5-yl, tetrahydrofuran-2-on-5-yl, 1,3-dithian-2-yl, tetrahydro-1,3-oxazin-2-yl or oxazolidin-2-yl.

4. Compounds of formula I in which
Y is oxygen;
$Q_1$ and $Q_2$ are each hydrogen;
$R_1$ and $R_2$ are each hydrogen;
$X_1$ is hydrogen, fluorine, chlorine, methyl, methoxy, phenyl, phenoxy, or phenyl or phenoxy each substituted by fluorine or by methyl;
$X_2$ is hydrogen, fluorine or chlorine;
$X_3$ is hydrogen;
A represents the bridge members,

ethenylene and ethynylene;
$R_3$ is methyl, ethyl, allyl, hydroxy, methoxy or ethoxy;
$R_4$ is hydrogen, methyl, ethyl, methoxy or ethoxy;
$W_1$ is cyclopentyl or cyclohexyl;
$W_2$ is 1,3-dioxolan-2-yl, 1,3-dioxan-2-yl, 1,3-dioxolan-4-on-5-yl, tetrahydrofuran-2-on-5-yl, 1,3-dithian-2-yl, tetrahydro-1,3-oxazin-2-yl or oxazolidin-2-yl.

5. Compounds of formula I in which
Y is oxygen;
$Q_1$ and $Q_2$ are each hydrogen;
$R_1$ and $R_2$ are each hydrogen; $X_1$ is hydrogen, fluorine, chlorine or methyl;
$X_2$ is hydrogen, fluorine or chlorine;
$X_3$ is hydrogen;
A represents the bridge member

$R_3$ is methyl, ethyl, n-propyl, i-propyl, n-butyl, allyl, methoxy or ethoxy;
$R_4$ is hydrogen, methyl or ethyl.

The following compounds are distinguished by especially advantageous plant-protecting properties:
[benzo-1,2,3-thiadiazole-7-carbonyloxymethyl]-2',4'-dichlorophenylketone (Comp. No. 1.2);
2-[benzo-1,2,3-thiadiazole-7-carbonyloxymethyl]-1-phenylcyclopropane (Comp. No. 2.1);
1-[benzo-1,2,3-thiadiazole-7-carbonyloxymethyl]-1-(4-methoxyphenyl)cyclopentane (Comp. No. 2.6);

2-[benzo-1,2,3-thiadiazole-7-carbonyloxymethyl]-1-phenylcyclopropane (Comp. No. 2.11);
3-[benzo-1,2,3-thiadiazole-7-carbonyloxymethyl]-1-phenyl-1-propene (Comp. No. 3.1);
2-[benzo-1,2,3-thiadiazole-7-carbonyloxy]-1-phenyl-n-propene (Comp. No. 4.1);
2-[benzo-1,2,3-thiadiazole-7-carbonyloxy]-1-phenyl-ethanol (Comp. No. 4.16 );
2-[benzo-1,2,3-thiadiazole-7-carbonyloxymethyl]-1-phenylpropionic acid methyl ester (Comp. No. 4.23);
1-[benzo-1,2,3-thiadiazole-7-carbonyloxy]-2-phenyl-n-propane (Comp. No. 4.4);
1-[benzo-1,2,3-thiadiazole-7-carbonyloxy]-2-phenyl-n-butane (Comp. No. 4.5);
1-[benzo-1,2,3-thiadiazole-7-carbonyloxy]-2-(2',4'-dichlorophenyl)-n-butane (Comp. No. 4.6);
1-[6-fluorobenzo-1,2,3-thiadiazole-7-carbonyloxy]-2-(2',4'-dichlorophenyl)-n-butane (Comp. No. 6.12).

It has now surprisingly been found that the use of compounds of formula I of the invention prevents plants from being attacked by harmful microorganisms and thus guards against damage to plants caused by such attack. A characteristic of the active ingredients of the invention is that the protection of the plants can stem both from the direct action on the plant-damaging microorganisms by means of foliar application or soil application and from the activation and stimulation of the plant's own defence system (immunisation). The great advantage of the compounds of formula I is that it is possible to ensure the continued health of plants treated with these substances also through their own resources without using further microbicidal substances during the vegetation period. Consequently it is possible by using the active ingredients of the invention to avoid the adverse side effects that may occur with direct parasite control using chemical substances, for example on the one hand as a result of damage to the useful plants (phytotoxicity) and on the other hand as a result of causing the harmful microorganisms to develop a resistance; consequently growth of the useful plants is advantageously completely undisturbed.

Owing to the double action of the compounds of formula I of the invention, that is to say on the one hand the direct control of the plant pathogens and on the other hand the increase in the general capacity of plants treated with these active ingredients to defend themselves as a result of immunisation, it is possible to achieve a broadly based protection of plants against disease. The use of the active ingredients of the invention is therefore especially suitable for practical application. Furthermore, the systemic activity peculiar to the compounds of formula I results in the protective effect being extended also to growing parts of the treated plants.

The generally plant-protecting activity of the active ingredients of the invention is effective, for example, against the phytopathogenic fungi belonging to the following classes: Fungi imperfecti (for example Botrytis, Helminthosporium, Fusarium, Septoria, Cercospora and Alternaria); Basidiomycetes (for example of the genera Hemileia, Rhizocotonia, Puccinia); Ascomycetes (for example Venturia, Podosphaera, Erysiphe, Monilinia, Uncinula).

In addition, the active ingredients can be used with particular advantage against the following harmful organisms:
fungi, such as, for example, Oomycetes (for example *Plasmopara viticola, Phytophthora infestans, Peronospora tabacina*, Pseudoperonospora, *Bermia letucae*), Fungi imperfecti (for example *Colletotrichum lagenarium, Piricularia oryzae, Cercospora nicotinae*), Ascomycetes (for example *Venturia inaequalis*);
bacteria, such as, for example, Pseudomonads (*Pseudomonas lachrymans, Pseudomonas tomato, Pseudomonas tabaci*); Xanthomanads (for example *Xanthomonas oryzae, Xanthomonas vesicatoria*); Erwinia (for example *Erwinia amylovora*); and viruses, such as, for example, the Tobacco Mosaic Virus.

The compounds of the invention can be used to protect plants of various useful crops.

The following species of plants, for example, are suitable for the use within the scope of the invention of compounds of formula I of the invention: cereals (wheat, barley, rye, oats, rice, sorghum and related crops); beet (sugar beet and fodder beet); pomes, drupes and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (cucumber, pumpkin, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocados, cinnamon, camphor), or plants such as maize, tobacco, nuts, coffee, sugar cane, tea, vines, hops, bananas and natural rubber plants, as well as ornamentals (flowers, shrubs, deciduous trees and conifers). This list does not constitute a limitation.

The following plants are to be regarded as especially suitable target crops for the application of the process of the invention: cucumber, tobacco, vines, rice, pepper, potatoes, tomatoes, wheat, barley, pears and apples.

The compounds of formula I are prepared as follows:
a) Reaction of an activated carboxylic acid derivative of formula II

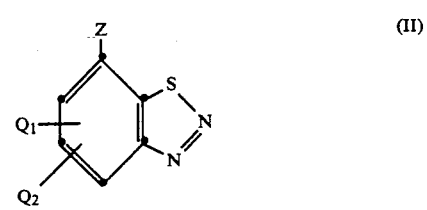

with an alcohol or thiol of formula III

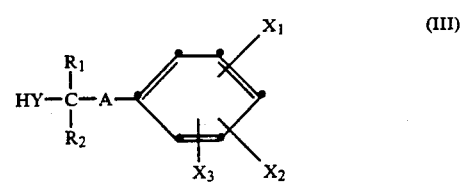

in the presence of a base and optionally with a catalyst, such as, for example, 4-dimethylaminopyridine, in an inert solvent, at temperatures of from −20° to 160° C., preferably −10° to 100° C., in which formulae Z represents the radicals Hal-CO,

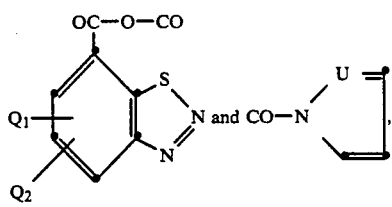

U is CH or N and Hal is halogen.

b) Reaction of the free acid of formula II'

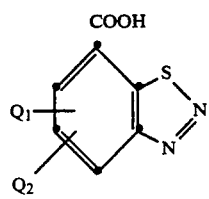

with an alcohol or thiol of formula III in the presence of an acidic catalyst, such as, for example, sulfuric acid, gaseous hydrogen chloride or hydrogen bromide or boron trifluoride etherate, in an inert solvent, such as, for example, dioxane, tetrahydrofuran or toluene, or in an excess of the alcohol or thiol component of formula III used for the esterification, at temperatures of from 10° to 180° C., preferably 0° to 120° C.

According to a further process, the preparation of compounds of formula I in which A is a carbonyl group is carried out as follows:

Reaction of the free carboxylic acid of formula II"

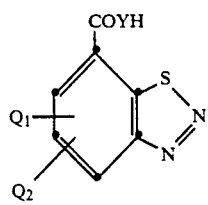

or an alkali salt or the silver salt thereof with an alkylating agent of formula IV

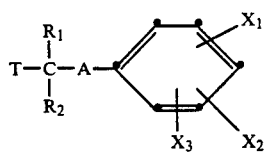

if appropriate with the addition of a catalyst, such as, for example, a quaternary ammonium salt, under phase transfer conditions (cf. in this respect W. E. Keller, Phasentransfer Reactions, Vol. 1, p. 68; Thieme-Verlag Stuttgart 1986), in which T is a leaving group, such as, for example, a halogen atom (F, Cl, Br, I) the methanesulfonyl radical, the toluenesulfonyl radical or the trifluoromethanesulfonyl radical.

According to a special arrangement of this process for the preparation of compounds of formula I, the free acid of formula II' is reacted with an alkylating agent of formula IV in the presence of potassium fluoride in a dipolar aprotic solvent, such as, for example, N,N-dimethylformamide, dimethyl sulfoxide, N-methylpyrrolidone or tetramethylurea.

In the preparation processes described above, the radicals or symbols A, $Q_1$, $Q_2$, $R_1$, $R_2$, $X_1$, $X_2$, $X_3$ and Y appearing therein are as defined for formula I.

Suitable bases are organic and inorganic bases, for example tertiary amines, such as trialkylamines (trimethylamine, triethylamine, tripropylamine etc.), pyridine bases (pyridine, 4-dimethylaminopyridine, 4-pyrrolidylaminopyridine, collidine), oxides and hydroxides, carbonates and hydrogen carbonates of alkali metals and alkaline earth metals, and also alkali acetates.

Suitable solvents and diluents that are inert towards the reactions are used as reaction media in accordance with the respective reaction conditions. The following may be mentioned as examples: aliphatic and aromatic hydrocarbons, such as benzene, toluene, xylenes, petroleum ether; halogenated hydrocarbons, such as chlorobenzene, methylene chloride, ethylene chloride, chloroform, carbon tetrachloride, tetrachloroethylene; ethers and ethereal compounds, such as dialkyl ethers (diethyl ether, diisopropyl ether, tert.-butyl methyl ether etc.), anisole, dioxane, tetrahydrofuran; nitriles, such as acetonitrile, propionitrile; N,N-dialkylated amides, such as dimethyformamide; ketones, such as acetone, diethyl ketone, methyl ethyl ketone; and also mixtures of such solvents with one another.

The alcohols or thiols of formula III used as starting compounds and also compounds of formula IV are mostly known or can be prepared according to methods known to the person skilled in the art, as described, for example, in the following:

J. Org. Chem. 33 2712 (1968); ibid 30, 23 (1964), ibid 31, 876 (1966), ibid 39, 1265 (1974), "Organosilicon compounds", V. Bažant et al. Academic Press New York 1965, Vol. 1 and 2; L. Zirngibl in "Progress in Drug Research Vol. 27, 253 (1983); Houben-Weyl, Vol. 9, p. 3.

The microbicidal compositions that are used within the scope of the invention for protecting plants against disease and that contain the compounds of formula I as active ingredients are to be considered as part of the invention.

The active ingredients of formula I are normally used in the form of compositions and can be applied to the plant or the locus thereof, simultaneously or in succession, with further active ingredients. These further active ingredients can be fertilisers or micronutrient donors or other preparations that influence plant growth. They can, however, also be selective herbicides, insecticides, fungicides, bactericides, nematicides, molluscicides or mixtures of several of these preparations, if desired together with further carriers, surfactants or other application-promoting adjuvants customarily employed in the art of formulation.

Suitable carriers and adjuvants can be solid or liquid and correspond to the substances ordinarily employed in formulation technology, e.g. natural or regenerated mineral substances, solvents, dispersants, wetting agents, tackifiers, thickeners, binders or fertilisers.

One method of applying an active ingredient of formula I or an agrochemical composition containing at least one of those active ingredients is application to the plant (foliar application). The active ingredients of formula I can, however, also penetrate the plant through the roots via the soil (soil application) if the locus of the plant is impregnated with a liquid formulation, or if the compounds are applied in solid form to the soil, for example in granular form. The compounds of formula I may, however, also be applied to seeds (coating), either by impregnating the seeds with a liquid formulation of the active ingredient or coating them with a solid formulation (dressing). In addition, in special cases further types of application are possible, for example the selective treatment of the plant stems or buds.

The compounds of formula I are used in unmodified form or, preferably, together with the adjuvants conventionally employed in the art of formulation, and are for this purpose formulated in known manner e.g. into emulsifiable concentrates, coatable pastes, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering, coating or pouring, are chosen in accordance with the intended objectives and the prevailing circumstances. Advantageous rates of application are normally from 50 g to 5 kg of active ingredient (a.i.) per hectare, preferably from 100 g to 2 kg a.i./ha, most preferably from 100 g to 600 g a.i./ha.

The formulations, i.e. the compositions, preparations or mixtures containing the compound (active ingredient) of formula I and, where appropriate, a solid or liquid adjuvant, are prepared by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils, such as epoxidised coconut oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are, for example, calcite or sand. In addition, a great number of pregranulated materials of inorganic or organic nature can be used, e.g. especially dolomite or pulverised plant residues.

Depending on the nature of the active ingredient of formula I to be formulated, suitable surface-active compounds are non-ionic, cationic and/or anionic surfactants having good emulsifying, dispersing and wetting properties. The term "surfactants" will also be understood as comprising mixtures of surfactants.

Cationic surfactants are especially quaternary ammonium salts that contain as N-substituent at least one alkyl radical having from 8 to 22 carbon atoms and as further substituents lower, unsubstituted or halogenated alkyl, benzyl or hydroxy-lower alkyl radicals.

Both so-called water-soluble soaps and also water-soluble synthetic surface-active compounds are suitable anionic surfactants.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid or of natural fatty acid mixtures which can be obtained e.g. from coconut oil or tallow oil.

Suitable synthetic surfactants are especially fatty alcohol sulfonates, fatty alcohol sulfates, sulfonated benzimidazole derivatives or alkylsulfonates. The fatty alcohol sulfonates or sulfates are usually in the form of alkali metal salts, alkaline earth metal salts or unsubstituted or substituted ammonium salts and contain an alkyl radical having from 8 to 22 carbon atoms.

Non-ionic surfactants are preferably polyglycol ether derivatives of aliphatic or cycloaliphatic alcohols, saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

The compositions may also contain further auxiliaries, such as stabilisers, antifoams, viscosity regulators, binders, tackifiers as well as fertilisers or other active ingredients for achieving special effects.

The agrochemical compositions usually contain 0.1 to 99% by weight, preferably 0.1 to 95% by weight, of a compound of formula I, 99.9 to 1% by weight, preferably 99.8 to 5% by weight, of a solid or liquid adjuvant, and 0 to 25% by weight, preferably 0.1 to 25% by weight, of a surfactant.

The following Examples serve to illustrate the invention without implying any limitation.

1. PREPARATION EXAMPLES

1.1 Preparation of 1-[benzo-1,2,3-thiadiazole-7-carbonyloxymethyl]-1-phenylcyclopropane

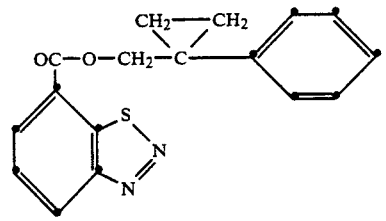

A solution of 6.7 g of benzo-1,2,3-thiadiazole-7-carboxylic acid chloride in 33 ml of dichloromethane is added dropwise at a maximum of 15° C., with cooling, to a solution of 5.0 g of 1-phenylcyclopropanemethanol, 6.1 ml of triethylamine and 200 mg of 4-dimethylaminopyridine in 50 ml of dichloromethane. The mixture is stirred overnight at room temperature until the reaction is complete, dichloromethane and ice-water are added, the aqueous phase is extracted with dichloromethane, and the organic phase is washed with water and NaCl solution, dried over $Na_2SO_4$ and concentrated by evaporation. The residue is purified on silica gel (hexane-ethyl acetate 1:1) and the product obtained is recrystallised from diethyl ether/hexane. 7.5 g of crystals having a melting point of 55°–57° C. are obtained.

1.2 Preparation of [benzo-1,2,3-thiadiazole-7-carbonyloxymethyl]-2',4'-dichlorophenylketone

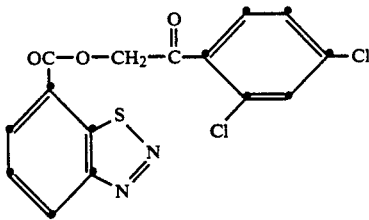

4 g of benzo-1,2,3-thiadiazole-7-carboxylic acid are added in portions to a suspension of 4 g of ω-bromo-2,4-dichloroacetophenone and 1.9 g of potassium fluoride in 15 ml of N,N-dimethylformamide and the mixture is stirred overnight at room temperature. Ice-water is then added, extraction is carried out with dichloromethane, and the extracts are washed with water, dried and concentrated by evaporation. After removal of the N,N-dimethylformamide in vacuo (1.3 Pa/40° C.), the residue is purified on silica gel (hexane/ethyl acetate/dichloromethane 6:2:1), yielding the title compound with a melting point of 136° C.

1.3 Preparation of 3-[benzo-1,2,3-thiadiazole-7-carbonyloxy]-1-phenyl-1-propene

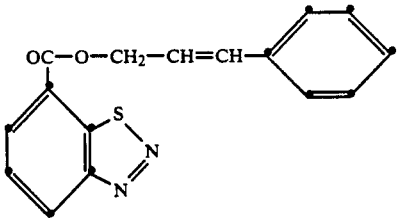

3 g of benzo-1,2,3-thiadiazole-7-carboxylic acid chloride in 25 ml of dichloromethane are added dropwise at 15° C., with cooling and stirring, to a solution of 2.3 g of cinnamic alcohol, 3.5 g of triethylamine and a spatula tip of 4-dimethylaminopyridine in 13 ml of dichloromethane, the mixture is stirred for 16 hours at room temperature, ice-water is added, and the aqueous phase is extracted with dichloromethane. The extracts are washed with water, dried over Na$_2$SO$_4$ and concentrated by evaporation. The solid residue is triturated with a small amount of diethyl ether, yielding the title compound with a melting point of 70°–72° C.

TABLE 1

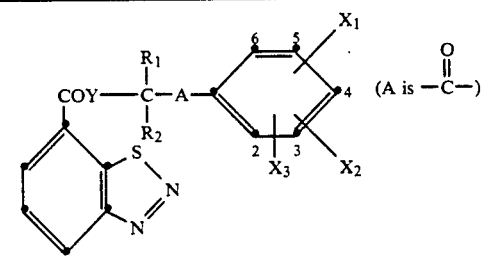

| Comp. No. | Y | R$_1$ | R$_2$ | X$_1$ | X$_2$ | X$_3$ | physical data |
|---|---|---|---|---|---|---|---|
| 1.1 | O | H | H | 2-OCH$_3$ | H | H | m.p. 159–161° C. |
| 1.2 | O | H | H | 2-Cl | 4-Cl | H | m.p. 136° C. |
| 1.3 | O | H | H | 4-Cl | H | H | m.p. 160° C. |
| 1.4 | O | CH$_3$ | H | H | H | H | m.p. 143–145° C. |
| 1.5 | O | CH$_3$ | CH$_3$ | H | H | H | m.p. 138–139° C. |
| 1.6 | O | C$_2$H$_5$ | H | H | H | H | |
| 1.7 | O | C$_3$H$_7$-n | H | H | H | H | |
| 1.8 | O | C$_4$H$_9$-n | H | H | H | H | |
| 1.9 | S | C$_4$H$_9$-t | H | H | H | H | |
| 1.10 | S | H | H | H | H | H | |
| 1.11 | S | C$_3$H$_7$-n | C$_3$H$_7$-n | 2-Cl | 4-Cl | 6-Cl | |
| 1.12 | S | H | H | 2-F | 4-Cl | H | |
| 1.13 | O | H | H | 2-CH$_3$ | H | H | |
| 1.14 | O | H | H | 3-F | H | H | |
| 1.15 | O | H | H | 3-CN | H | H | |
| 1.16 | O | H | H | 3-CF$_3$ | H | H | |
| 1.17 | O | C$_4$H$_9$-n | C$_4$H$_9$-n | 4-C$_4$H$_9$-t | H | H | |
| 1.18 | O | H | H | 4-OCF$_3$ | H | H | |
| 1.19 | O | H | H | 2-OCF$_2$CF$_3$ | H | H | |

TABLE 1-continued

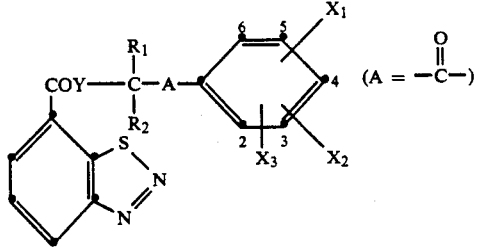

(A = −C(=O)−)

| Comp. No. | Y | R₁ | R₂ | X₁ | X₂ | X₃ | physical data |
|---|---|---|---|---|---|---|---|
| 1.20 | S | H | H | 4-N(CH₃)₂ | H | H | |
| 1.21 | O | CH₃ | H | 4-N(CH₃)₂ | H | H | |
| 1.22 | O | CH₃ | CH₃ | 3-N(CH₃)₂ | H | H | |
| 1.23 | O | H | H | 2-CH₃ | 4-Cl | H | |
| 1.24 | O | H | H | 3-Cl | 5-Cl | H | |
| 1.25 | O | H | H | 2-Cl | 4-[4'-Cl Phenoxy] | H | m.p. 122–124° C. |
| 1.26 | O | H | H | 2-Br | 4-[4'-F-Phenoxy] | H | m.p. 136–137° C. |
| 1.27 | O | H | H | 2-CH₃ | 4-Phenoxy | H | m.p. 118–120° C. |
| 1.28 | O | H | H | 2-CH₃ | 4-[4'-Cl-Phenoxy] | H | m.p. 135–136° C. |
| 1.29 | S | H | H | 4-Phenoxy | H | H | |
| 1.30 | S | H | H | 4-Phenol | H | H | |
| 1.31 | O | H | H | 3-Phenol | H | H | |
| 1.32 | O | CH₃ | H | 4-Phenoxy | H | H | |
| 1.33 | O | CH₃ | CH₃ | 3-Phenol | H | H | |
| 1.34 | O | C₂H₅ | H | 4-[4'OCH₃-Phenoxy] | H | H | |
| 1.35 | S | H | H | 4-[2'OC₂H₅-Phenoxy] | H | H | |
| 1.36 | O | H | H | 4-OC₂H₅ | H | H | |
| 1.37 | O | CH₃ | CH₃ | 2-F | 4-F | 6-F | |
| 1.38 | O | CH₃ | C₂H₅ | 3-Cl | 4-Cl | H | |
| 1.39 | O | n-C₄H₉ | H | 4-Phenoxy | H | H | |
| 1.40 | O | H | H | 3-NO₂ | H | H | |

TABLE 2

| Comp. No. | Y | R₁ | R₂ | X₁ | X₂ | X₃ | A | physical data |
|---|---|---|---|---|---|---|---|---|
| 2.1 | O | H | H | H | H | H | (cyclopropyl) | m.p. 55–57° C. |
| 2.2 | O | H | H | 2-Cl | 4-Cl | H | −C(=O)−O−C(CH₃)₂−O− | m.p. 156–158° C. |
| 2.3 | O | H | H | 2-Cl | 4-Cl | H | −C(=O)−O−C(CH₃)₂−CH(CH₃)− | m.p. 201–203° C. |

TABLE 2-continued
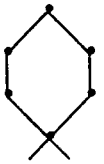
| Comp. No. | Y | R₁ | R₂ | X₁ | X₂ | X₃ | A | physical data |
|---|---|---|---|---|---|---|---|---|
| 2.4 | O | H | H | 4-OCH₃ | H | H | 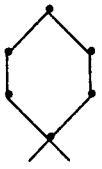 | m.p.105–107° C. |
| 2.5 | O | H | H | 2-Cl | 4-Cl | H | 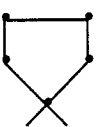 | m.p.130–134° C. |
| 2.6 | O | H | H | 4-OCH₃ | H | H |  | m.p.62–64° C. |
| 2.7 | O | H | H | 4-Br | H | H |  | m.p.103–104° C. |
| 2.8 | O | H | H | 4-F | H | H |  | m.p.103–104° C. |
| 2.9 | O | H | H | 4-OC₂H₅ | H | H |  | m.p.64–68° C. |
| 2.10 | O | H | H | 4-OC₂H₅ | H | H |  | m.p.100–102° C. |
| 2.11 | S | H | H | H | H | H |  | |
| 2.12 | O | H | H | 4-Cl | H | H |  | |

TABLE 2-continued
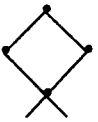
| Comp. No. | Y | R₁ | R₂ | X₁ | X₂ | X₃ | A | physical data |
|---|---|---|---|---|---|---|---|---|
| 2.13 | O | H | H | 2-Cl | 4-Cl | H |  | |
| 2.14 | S | H | H | —C₄H₉-t | H | H | 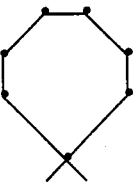 | |
| 2.15 | O | H | H | H | H | H | 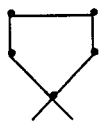 | |
| 2.16 | S | H | H | H | H | H | 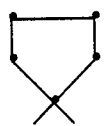 | |
| 2.17 | O | H | H | 4-Cl | H | H | 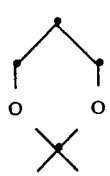 | |
| 2.18 | O | H | H | 2-Cl | 4-Cl | H | 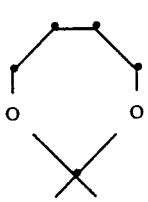 | |
| 2.19 | O | H | H | 2-F | H | H | 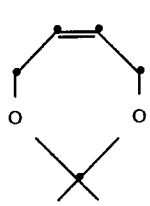 | |
| 2.20 | S | H | H | H | H | H |  | |

TABLE 2-continued
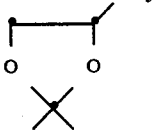
| Comp. No. | Y | $R_1$ | $R_2$ | $X_1$ | $X_2$ | $X_3$ | A | physical data |
|---|---|---|---|---|---|---|---|---|
| 2.21 | O | H | H | 2-Cl | 4-Cl | H | 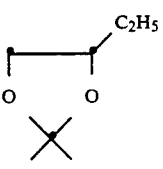 | |
| 2.22 | O | H | H | 2-Cl | 4-Cl | H | 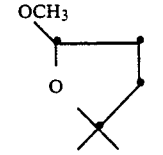 | |
| 2.23 | O | H | H | 4-Cl | H | H | 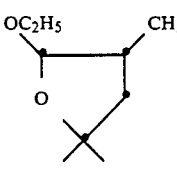 | |
| 2.24 | S | H | H | 2-Cl | 4-Cl | H | 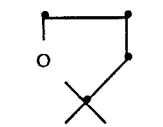 | |
| 2.25 | O | H | H | H | H | H | 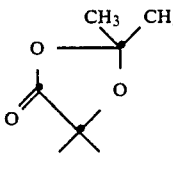 | |
| 2.26 | O | H | H | 2-Cl | 4-Cl | H | 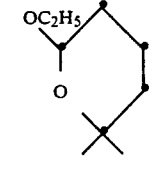 | |
| 2.27 | O | H | H | 2-Cl | 4-Cl | H | 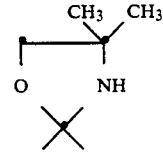 | |
| 2.28 | O | H | H | H | H | H |  | |

TABLE 2-continued
| Comp. No. | Y | R₁ | R₂ | X₁ | X₂ | X₃ | A | physical data |
|---|---|---|---|---|---|---|---|---|
| 2.29 | O | H | H | H | H | H |  | |
| 2.30 | O | H | H | H | H | H |  | |
| 2.31 | S | H | H | 2-Cl | 4-Cl | H |  | |
| 2.32 | O | CH₃ | H | H | H | H | 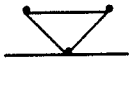 | |
| 2.33 | O | H | H | 2-Cl | 4-Cl | 6-Cl |  | |
| 2.34 | O | CH₃ | CH₃ | H | H | H |  | |
| 2.35 | O | C₄H₉-n | H | 2-Cl | 4-Cl | H | 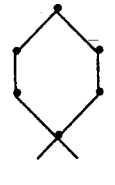 | |
| 2.36 | S | C₃H₇-i | H | H | H | H | 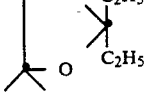 | |
| 2.37 | O | H | H | 2-Phenyl | H | H | 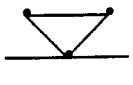 | |

TABLE 2-continued

| Comp. No. | Y | R₁ | R₂ | X₁ | X₂ | X₃ | A | physical data |
|---|---|---|---|---|---|---|---|---|
| 2.38 | O | H | H | 3-O-Phenyl | H | H | | |
| 2.39 | O | H | H | 2-CH₃ | 4-Cl-OPhenyl | H | | |
| 2.40 | O | H | H | 2-CH₃ | 4-Cl-OPhenyl | H | | |
| 2.41 | O | H | H | 2-Cl | 4-Cl-OPhenyl | H | | |
| 2.42 | S | C₂H₅ | H | 4-Phenyl | H | H | | |
| 2.43 | O | H | H | H | H | H | | |
| 2.44 | O | C₃H₇-n | C₃H₇-n | H | H | H | | |
| 2.45 | O | H | H | H | H | H | | |

TABLE 2-continued

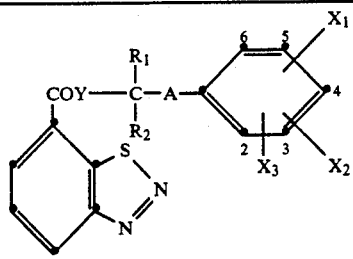

| Comp. No. | Y | R₁ | R₂ | X₁ | X₂ | X₃ | A | physical data |
|---|---|---|---|---|---|---|---|---|
| 2.46 | O | H | H | H | H | H | 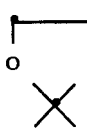 C₄H₉-n | |

TABLE 3

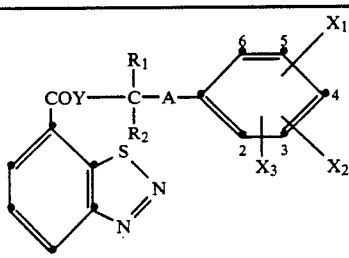

| Comp. No. | Y | R₁ | R₂ | X₁ | X₂ | X₃ | A | physical data |
|---|---|---|---|---|---|---|---|---|
| 3.1 | O | H | H | H | H | H | —CH=CH— | m.p.70–72° C. |
| 3.2 | O | H | H | H | H | H | —C≡C— | |
| 3.3 | O | H | H | 2-CH₃ | H | H | —CH=CH— | |
| 3.4 | O | H | H | 2-OCH₃ | H | H | —CH=CH— | |
| 3.5 | O | H | H | 3-NO₂ | H | H | —CH=CH— | |
| 3.6 | O | H | H | 3-CF₃ | H | H | —CH=CH— | |
| 3.7 | O | H | H | 4-OCF₃ | H | H | —CH=CH— | |
| 3.8 | O | H | H | 4-N(CH₃)₂ | H | H | —CH=CH— | |
| 3.9 | O | CH₃ | H | 2-Cl | H | H | —CH=CH— | |
| 3.10 | O | CH₃ | H | 2-Cl | 4-Cl | H | —CH=CH— | |
| 3.11 | O | CH₃ | CH₃ | 2-Cl | 4-Cl | 6-Cl | —CH=CH— | |
| 3.12 | O | C₄H₉-n | C₄H₉-n | 3-Cl | 5-Cl | H | —CH=CH— | |
| 3.13 | S | H | H | H | H | H | —CH=CH— | |
| 3.14 | S | C₄H₉-n | H | 4-OCH₃ | H | H | —CH=CH— | |
| 3.15 | S | H | H | H | H | H | —C≡C— | |
| 3.16 | O | H | H | 3-CN | H | H | —CH=CH— | |
| 3.17 | O | H | H | 4-OPhenyl | H | H | —CH=CH— | |
| 3.18 | O | H | H | 4-Phenyl | H | H | —CH=CH— | |
| 3.19 | O | H | H | 3-Phenyl | H | H | —CH=CH— | |
| 3.20 | O | H | H | 2-CH₃ | 4-O-Phenyl | H | —CH=CH— | |

TABLE 4

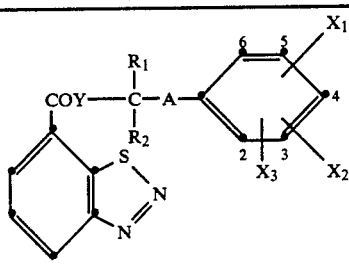

| Comp. No. | Y | R₁ | R₂ | X₁ | X₂ | X₃ | A | physical data |
|---|---|---|---|---|---|---|---|---|
| 4.1 | O | CH₃ | H | H | H | H | —CH₂— | $n_D^{25}$ 1.5932 |

TABLE 4-continued

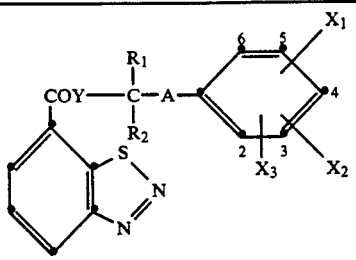

| Comp. No. | Y | R₁ | R₂ | X₁ | X₂ | X₃ | A | physical data |
|---|---|---|---|---|---|---|---|---|
| 4.2 | O | CH₃ | CH₃ | H | H | H | —CH₂— | |
| 4.3 | O | CH₃ | CH₃ | H | H | H | —CH(CH₃)— | |
| 4.4 | O | H | H | H | H | H | —CH(CH₃)— | n_D²⁵ 1.6000 |
| 4.5 | O | H | H | H | H | H | —CH(C₂H₅)— | n_D²⁵ 1.5958 |
| 4.6 | O | H | H | 2-Cl | 4-Cl | H | —CH—(C₃H₇-n)— | n_D²⁵ 1.5876 |
| 4.7 | O | H | H | H | H | H | —CH—(C₄H₉-n)— | |
| 4.8 | S | H | H | H | H | H | —CH—(C₄H₉-i)— | |
| 4.9 | O | H | H | H | H | H | —CH—(C₄H₉-t)— | |
| 4.10 | O | H | H | H | H | H | —CH—(n-Pentyl)- | |
| 4.11 | S | H | H | H | H | H | —CH—(n-Hexyl)- | |
| 4.12 | O | H | H | 2-Cl | 4-Cl | H | —CH-(Allyl) | |
| 4.13 | O | C₄H₉-n | H | 2-Cl | H | H | —CH—(2-Butenyl)- | |
| 4.14 | S | H | H | 2-F | 4-F | H | —C(CH₃)₂— | |
| 4.15 | O | H | H | 2-Cl | 4-Cl | H | —C(CN)(C₄H₉-n) | |
| 4.16 | O | H | H | H | H | H | —CH(OH)— | |
| 4.17 | O | H | H | 2-Cl | 4-Cl | H | —C(OH)(n-Pr)- | |
| 4.18 | O | H | H | 2-Cl | 4-Cl | 6-Cl | —CH(OCH₃)— | |
| 4.19 | O | H | H | 2-Cl | 4-Cl | H | —C(OCH₃)(C₃H₇-n)— | |
| 4.20 | S | C₃H₇-n | H | H | H | H | —CH(n-Hexyl)- | |
| 4.21 | O | H | H | 2-Cl | 4-Cl | H | —CH(OH)— | |
| 4.22 | O | H | H | H | H | H | —CH(COOH)— | |
| 4.23 | O | H | H | H | H | H | —CH(COOCH₃)— | |
| 4.24 | O | H | H | H | H | H | —CH(COO C₄H₉-n)— | |
| 4.25 | O | H | H | H | H | H | —CH(COO C₃H₇-n)— | |
| 4.26 | O | H | H | 2-F | H | H | —CH[OC(O)CH₃]— | |
| 4.27 | O | H | H | H | H | H | —CH[OC(O)C₄H₉-i]— | |
| 4.28 | O | CH₃ | H | H | H | H | —C(OCH₃)₂— | |
| 4.29 | O | H | H | H | H | H | —C(OC₂H₅)₂— | |
| 4.30 | O | H | H | H | H | H | —C(OC₄H₉-n)₂— | |
| 4.31 | O | H | H | H | H | H | —C(O-sec-C₆H₁₃)₂— | |
| 4.32 | O | H | H | 2-Cl | 4-Cl | H | —CH(COOCH₃)— | |
| 4.33 | O | H | H | 2-Cl | 4-Cl | H | —CH(COO—C₃H₇-n)— | |
| 4.34 | O | H | H | 2-Cl | 4-Cl | H | —CH[OC(O)CH₃]— | |
| 4.35 | O | H | H | 2-Cl | 4-F | H | —C(OC₄H₉-n)₂— | |
| 4.36 | S | C₄H₉-n | H | H | H | H | —CH(COOC₂H₅)— | |
| 4.37 | O | CH₃ | CH₃ | H | H | H | —C(OC₂H₅)₂— | |
| 4.38 | O | H | H | 2-Phenyl | H | H | —CH(COO C₃H₇-n)— | |
| 4.39 | O | H | H | 4-Phenyl | H | H | —C(OH)(COOCH₃)— | |
| 4.40 | O | H | H | 2-Cl | 4-Cl | H | C(OH)(COO C₃H₇-n)— | |
| 4.41 | O | H | H | 4-OPhenyl | H | H | —C(OC₃H₇-n)₂— | |
| 4.42 | S | H | H | 2-CH₃ | 4-NO₂ | H | CH(COOCH₃)— | |

TABLE 5
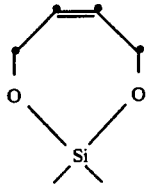
| Comp. No. | Y | R₁ | R₂ | X₁ | X₂ | X₃ | A | physical data |
|---|---|---|---|---|---|---|---|---|
| 5.1 | O | H | H | H | H | H | 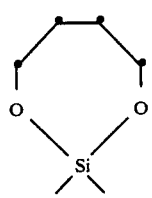 | |
| 5.2 | O | H | H | H | H | H | 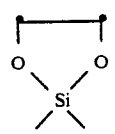 | |
| 5.3 | O | CH₃ | H | 2-Cl | 4-Cl | H | 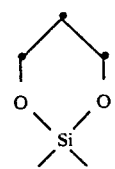 | |
| 5.4 | O | H | H | 4-F | H | H | 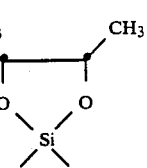 | |
| 5.5 | S | H | H | 4-OCH₃ | H | H | 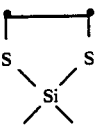 | |
| 5.6 | O | C₂H₅ | C₂H₅ | 2-Cl | 4-Cl | 6-Cl | 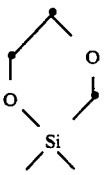 | |
| 5.7 | O | C₄H₉-n | H | H | H | H |  | |

TABLE 5-continued
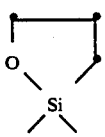
| Comp. No. | Y | R₁ | R₂ | X₁ | X₂ | X₃ | A | physical data |
|---|---|---|---|---|---|---|---|---|
| 5.8 | O | CH₃ | H | H | H | H | 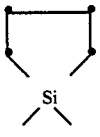 | |
| 5.9 | O | H | H | H | H | H | 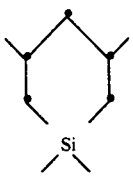 | |
| 5.10 | O | H | H | 4-F | H | H | 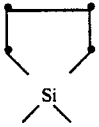 | |
| 5.11 | O | CH₃ | H | 4-F | H | H | (same 5-ring Si group) | |
| 5.12 | O | H | H | H | H | H | —Si(OC₂H₅)₂— | |
| 5.13 | O | H | H | H | H | H | —(CH₃Si(OCH₃)— | |
| 5.14 | O | H | H | H | H | H | -(Phenyl)Si(OC₂H₅)— | |
| 5.15 | S | H | H | H | H | H | -(Phenyl)Si(CH₃)— | |
| 5.16 | S | H | H | H | H | H | -(Phenyl)Si(C₃H₇-n)— | |
| 5.17 | O | H | H | 4-F | H | H | -(2'-F-Phenyl)Si(CH₃)— | |
| 5.18 | O | H | H | 4-F | H | H | -(4'-F-Phenyl)Si(OH)— | |
| 5.19 | O | CH₃ | H | H | H | H | —Si(OC₄H₉-n)₂— | |

TABLE 6

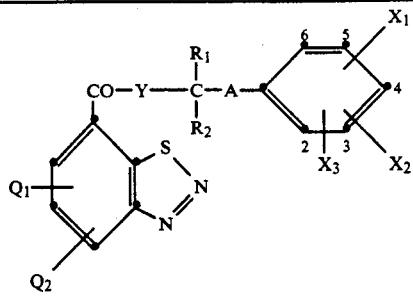

| Comp. No. | Y | Q₁ | Q₂ | R₁ | R₂ | X₁ | X₂ | X₃ | A | physical data |
|---|---|---|---|---|---|---|---|---|---|---|
| 6.1 | O | 5-Cl | H | H | H | 4-Cl | H | H | —C(O)— | |
| 6.2 | O | 5-F | H | CH₃ | H | 2-Cl | 4-Cl | H | —C(O)— | oil |
| 6.3 | O | 6-F | H | H | H | H | H | H | —C(O)— | |
| 6.4 | S | 4-F | H | CH₃ | CH₃ | H | H | H | —CH(OH)— | |
| 6.5 | O | 5-Br | H | H | H | H | H | H | —C(O)— | |
| 6.6 | O | 5-F | H | H | H | H | H | H | (cyclopropyl) | |
| 6.7 | O | 5-F | 6-F | H | H | H | H | H | (cyclopropyl) | |
| 6.8 | O | 5-I | H | C₂H₅ | H | 2-Cl | 4-Cl | 6-Cl | (dioxolane) | |
| 6.9 | O | 4-F | 5-F | H | H | H | H | H | (dioxane) | |
| 6.10 | O | 6-Cl | H | H | H | 2-CH₃ | 4-O-Phenyl | H | —CH=CH— | |
| 6.11 | O | 5-F | H | H | H | H | H | H | —C≡H— | |
| 6.12 | O | 6-F | H | H | H | 2-Cl | 4-Cl | H | —CH(C₃H₇-n)— | $n_D^{25}$ 1.5817 |
| 6.13 | S | 4-F | H | CH₃ | CH₃ | H | H | H | —C(OH)(C₄H₉-n)— | |
| 6.14 | O | 5-I | H | H | H | 2-Cl | 4-Cl | H | —C(OH)(COOCH₃)— | |
| 6.15 | S | 4-F | H | C₄H₉-n | H | H | H | H | (dithiolane) | |
| 6.16 | O | 4-F | H | H | H | 2-Cl | 4-Cl | H | —CH(C₃H₇-n)— | |
| 6.17 | O | 4-F | H | H | H | H | H | H | —CH(CH₃)— | |

FORMULATION EXAMPLES FOR ACTIVE INGREDIENTS OF FORMULA I (THROUGHOUT, PERCENTAGES ARE BY WEIGHT)

| 2.1 Wettable powders | a) | b) | c) |
|---|---|---|---|
| active ingredient from the Tables | 25% | 50% | 75% |
| sodium lignosulfonate | 5% | 5% | — |
| sodium laurylsulfate | 3% | — | 5% |
| sodium diisobutylnaphthalenesulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient is mixed with the adjuvants and the mixture is homogeneously ground in a suitable mill, affording wettable powders which can be diluted with water to give suspensions of the desired concentration.

| 2.2 Emulsifiable concentrate | |
|---|---|
| active ingredient from the Tables | 10% |
| octylphenol polyethylene glycol ether (4-5 moles of ethylene oxide) | 3% |
| calcium dodecylbenzenesulfonate | 3% |
| castor oil polyglycol ether (35 moles of ethylene oxide) | 4% |
| cyclohexanone | 30% |
| xylene mixture | 50% |

Emulsions of any required concentration can be obtained from this concentrate by dilution with water.

| 2.3 Dusts | a) | b) |
|---|---|---|
| an active ingredient from the Tables | 5% | 8% |
| talcum | 95% | — |
| kaolin | — | 92% |

Ready-for-use dusts are obtained by mixing the active ingredient with the carriers and grinding the mixture in a suitable mill.

| 2.4 Extruder granulate | |
|---|---|
| an active ingredient from the Tables | 10% |
| sodium lignosulfonate | 2% |
| carboxymethylcellulose | 1% |
| kaolin | 87% |

The active ingredient is mixed and ground with the adjuvants, and the mixture is moistened with water. The mixture is extruded and then dried in a stream of air.

| 2.5 Coated granulate | |
|---|---|
| an active ingredient from the Tables | 3% |
| polyethylene glycol (MW 200) | 3% |
| kaolin | 94% |

(MW = molecular weight)

The finely ground active ingredient is uniformly applied, in a mixer, to the kaolin moistened with polyethylene glycol. Non-dusty coated granulates are obtained in this manner.

| 2.6 Suspension concentrate | |
|---|---|
| an active ingredient from the Tables | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

3. BIOLOGICAL EXAMPLES

EXAMPLE 3.1

Action against *Colletotrichum lagenarium* on *Cucumis sativus* L.

a) After 2 weeks' cultivation, cucumber plants are sprayed with a spray mixture prepared from a wettable powder formulation of the test compound (concentration: 200 ppm). After 48 hours the plants are infected with a spore suspension ($1.5 \times 10^5$ spores/ml) of the fungus and incubated for 36 hours at high humidity and a temperature of 23° C. Incubation is then continued at normal humidity and at from 22° C. to 23° C.

The protective action is assessed on the basis of the fungal attack 7 to 8 days after infection.

b) After 2 weeks' cultivation, cucumber plants are treated by soil application with a spray mixture prepared from a wettable powder formulation of the test compound (concentration: 60 or 20 ppm based on the volume of soil). After 48 hours the plants are infected with a spore suspension ($1.5 \times 10^5$ spores/ml) of the fungus and incubated for 36 hours at high humidity and a temperature of 23° C. Incubation is then continued at normal humidity and at 22° C.

The protective action is assessed on the basis of the fungal attack 7 to 8 days after infection.

c) After 2 weeks' cultivation, cucumber plants are sprayed with a spray mixture prepared from a wettable powder formulation of the test compound (concentration: 200 ppm)

After 3 weeks the plants are infected with a spore suspension ($1.5 \times 10^5$ spores/ml) of the fungus and incubated for 36 hours at high humidity and a temperature of 23° C. Incubation is then continued at normal humidity and at from 22° to 23° C.

The protective action is assessed on the basis of the fungal attack 7 to 8 days after infection.

Compounds from Tables 1 to 6 exhibited good activity in tests (a) and (b). For example, compounds 1.2, 1.3, 1.4, 1.28, 2.1, 2.2, 2.5, 3.1 and 4.6 confined fungal attach to 0 to 20%. On the other hand, Colletotrichum attack was 100% on untreated and infected control plants.

EXAMPLE 3.2

Action against *Puccinia graminis* on wheat a) Wheat plants are sprayed 6 days after sowing with a spray mixture (0.02% active ingredient) prepared from a wettable powder formulation of the test compound. After 24 hours the treated plants are infected with a uredospore suspension of the fungus. The infected plants are incubated for 48 hours at 95-100% relative humidity and about 20° C. and then stood in a greenhouse at about 22° C. Evaluation of rust pustule development is made 12 days after infection.

b) 5 days after sowing, wheat plants are watered with a spray mixture (0.006% active ingredient based on the volume of soil) prepared from a wettable powder formulation of the test compound. After 48 hours the treated plants are infected with a uredospore suspension of the fungus. The infected plants are incubated for 48 hours at 95-100% relative humidity and about 20° C. and then stood in a greenhouse at about 22° C. Evaluation of rust pustule development is made 12 days after infection.

Compounds from Tables 1 to 6 exhibited good activity against Puccinia fungi. For example, compounds 1.1, 1.27, 2.2, 2.10, 3.1 and 4.6 confined fungal attack to 0 to 20%. On the other hand, Puccinia attack was 100% on untreated and infected control plants.

EXAMPLE 3.3

Action against Phytophthora infestans on tomato plants a) After 3 weeks' cultivation, tomato plants are sprayed with a spray mixture (0.02% active ingredient) prepared from a wettable powder formulation of the test compound. After 24 hours the treated plants are infected with a sporangia suspension of the fungus. The fungal attack is evaluated after incubating the infected plants for 5 days at 90–100% relative humidity and 20° C.

b) After a cultivation period of 3 weeks tomato plants are watered with a spray mixture (0.006% active ingredient based on the volume of soil) prepared from a wettable powder formulation of the test compound. Care is taken that the spray mixture does not come into contact with the parts of the plants that are above the soil. After 48 hours the treated plants are infected with a sporangia suspension of the fungus. The fungal attack is evaluated after incubating the infected plants for 5 days at 90–100% relative humidity and 20° C.

Compounds from Tables 1 to 6 exhibited a good protective action against the Phytophthora fungus. For example, compounds 1.1, 1.2, 1.3, 1.4, 1.5, 1.6, 1.25, 1.26, 1.28, 2.1, 2.5, 2.6, 3.1 and 4.6 confined fungal attack to 0 to 20%. On the other hand, Phytophthora attack was 100% on untreated and infected control plants.

EXAMPLE 3.4

Action against *Pyricularia oryzae* on rice plants a) After 2 weeks' cultivation, rice plants are sprayed with a spray mixture (0.02% active ingredient) prepared from a wettable powder formulation of the test compound. After 48 hours, the treated plants are infected with a conidia suspension of the fungus. Evaluation of fungal attack is made after incubation for 5 days at 95–100% relative humidity and 24° C.

b) 2 week-old rice plants are watered with a spray mixture (0.006% active ingredient based on the volume of soil) prepared from a wettable powder formulation of the test compound. The pots are then filled with water until the lowest parts of the stalks of the rice plants stand in water. After 96 hours the treated rice plants are infected with a conidia suspension of the fungus. Evaluation of fungal attack is made after incubation of the infected plants for 5 days at 95–100% relative humidity and approximately 24° C.

Rice plants that had been treated with a spray mixture containing one of the compounds from Tables 1 to 6 as active ingredient exhibited only slight fungal attack compared with untreated control plants (100% attack). For example in test (a) compounds 1.1, 1.2, 1.3, 1.5, 1.25, 1.27, 2.1, 2.2, 2.3, 2.5, 2.8, 3.1 and 4.6, and in test (b) compounds 1.2, 1.3, 2.1, 2.5, 2.6, 2.8 and 2.10 confined fungal attack to 0 to 20%.

EXAMPLE 3.5

Action against *Xanthomonas oryzae* on rice (*Oryza sativa*)

a) After 3 weeks' cultivation in a greenhouse, rice plants of the variety "Calora" or "S6" are sprayed with the test substance in the form of a spray mixture (0.02% active ingredient). After this spray coating has dried for 1 day the plants are placed in a climatic chamber at 24° C. and 75–85% relative humidity and infected. The infection is carried out by cutting off the leaf tips with shears that have beforehand been immersed in a suspension of *Xanthomonas oryzae*. After an incubation period of 10 days the cut leaves that have been attacked become shrivelled, roll up and become necrotic. The residual activity of the test substance is evaluated on the basis of the extent of these disease symptoms.

b) After a cultivation period of 3 weeks in a greenhouse, rice plants of the variety "Calora" or "S6" are watered with a suspension of the test substance (0.006% active ingredient based on the volume of soil). Three days after this treatment the plants are placed in a climatic chamber at 24° C. and 75–85% relative humidity and infected. The infection is carried out by cutting off the leaf tips with shears that have beforehand been immersed in a suspension of *Xanthomonas oryzae*. After an incubation period of 10 days the cut leaves that have been attacked become shrivelled, roll up and become necrotic. The systemic activity of the test substance is evaluated on the basis of the extent of these disease symptoms.

Compounds from Tables 1 to 6 exhibited a good protective action against *Xanthomonas oryzae*. For example in test (a) compounds 2.1 and 3.1, and in test (b) compound 3.1, confined bacterial attack to 0 to 20%. On the other hand, disease attack was 100% on untreated and infected control plants.

EXAMPLE 3.6

Action against *Xanthomonas vesicatoria* on paprika (*Capsicum annuum*)

a) After 3 weeks' cultivation in a greenhouse, paprika plants of the variety "California Wonder" are sprayed with the test substance in the form of a spray mixture (0.02% active ingredient). After the spray coating has dried for one day, the plants are placed in a climatic chamber at 26° C. and 95–100% relative humidity and infected by spraying the undersides of the leaves with a standardised suspension of *Xanthomonas vesicatoria*. After an incubation period of 6 days, round, initially watery, later necrotic, light specks form on the leaves attacked. The residual activity of the test substance is evaluated on the basis of the extent of these specks.

b) After a cultivation period of 3 weeks in a greenhouse, paprika plants of the variety "California Wonder" are watered with a suspension of the test substance (0.006% active ingredient based on the volume of soil) Three days after this treatment the plants are placed in a climatic chamber at 26° C. and 95–100% relative humidity and infected by spraying the undersides of the leaves with a standardised suspension of *Xanthomonas vesicatoria*. After an incubation period of 6 days, round, initially watery, later necrotic, light specks form on the leaves attacked. The systemic activity of the test substance is evaluated on the basis of the extent of these specks.

Compounds from Tables 1 to 6 exhibited a good protective action against *Xanthomonas vesicatoria*. For example in test (a) compounds 2.1, 2.2 and 3.1, and in test (b) compound 3.1, confined the bacterial attack to 0 to 20%. On the other hand, disease attack was 100% on untreated and infected control plants.

EXAMPLE 3.7

Action against *Pseudomonas tomato* on tomato plants a) After 3 weeks' cultivation tomato plants are treated by foliar application with a spray mixture prepared from a wettable powder formulation of the test compound (concentration: 200 ppm). After 3.5 weeks the plants are inoculated with a bacterial suspension ($10^8$ bacteria/ml) and incubated for 6 days at high humidity and at a temperature of 25° C. The protective action is evaluated 7 to 8 days after inoculation on the basis of the bacterial attack.

Attack is 100% in untreated and infected control plants in this test.

Compounds from Tables 1 to 6 exhibited a good protective action against *Pseudomonas tomato*. For example plants treated with compounds 2.1 or 3.1 were substantially free of Pseudomonas (0 to 20% attack).

b) After 3 weeks' cultivation tomato plants are treated by soil application with a spray mixture prepared from a wettable powder formulation of the test compound (concentration: 60 ppm based on the volume of soil). After 3.5 weeks the plants are inoculated with a bacterial suspension ($10^8$ bacteria/ml) and incubated for 6 days at high humidity and at a temperature of 25° C.

The protective action is evaluated 7 to 8 days after inoculation on the basis of the bacterial attack.

Attack is 100% in untreated and infected control plants in this test.

Compounds from Tables 1 to 6 exert a good action against *Pseudomonas tomato*. For example plants treated with compound 3.1 were almost completely free of Pseudomonas (0 to 20% attack).

EXAMPLE 3.8

Action against *Cercospora nicotianae* on tobacco plants a) Tobacco plants (8 weeks old) are sprayed with a formulated solution of the test compound (concentration: 200 ppm). Four days after the treatment the plants are inoculated with a spore suspension of *Cercospora nicotianae* (105 spores/ml) and incubated for 5 days at high humidity and a temperature of 22°-25° C. The incubation is then continued at normal humidity and at 20°-22° C.

b) Tobacco plants (8 weeks old) were treated with a formulated solution of the test compound by soil application (concentration: 0.002% of active ingredient). After 4 days the plants were inoculated with a spore suspension of *Cercospora nicotianae* (105 spores/ml) and incubated for 5 days at high humidity and a temperature of 22°-25° C. The incubation was then continued at normal humidity and at 20°-22° C.

Evaluation of the symptoms in tests (a) and (b) is effected on the basis of the fungal attack 12 to 14 days after infection.

Attack was 100% on the control plants. Attack was 0-20% on plants that had been treated with compound 2.1 in tests (a) and (b).

What is claimed is:

1. A compound of formula I

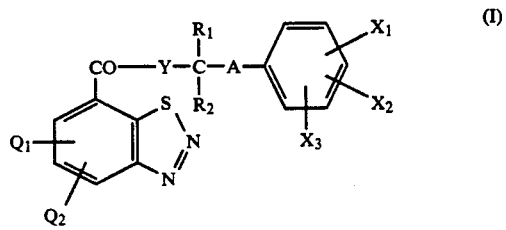

in which

Y is oxygen or sulfur;

$Q_1$ and $Q_2$ independently of one another are each hydrogen or halogen;

$R_1$ and $R_2$ independently of one another are each hydrogen or $C_1$-$C_4$alkyl;

$X_1$ is hydrogen, halogen, $C_1$-$C_4$alkyl, trifluoromethyl, $C_1$-$C_3$alkoxy, $C_1$-$C_2$alkoxy halo-substituted in the alkyl moiety, nitro, cyano, dimethylamino, phenyl, phenoxy, or phenyl or phenoxy each substituted by halogen and/or by $C_1$-$C_2$alkyl and/or by $C_1$-$C_2$alkoxy;

$X_2$ is hydrogen, halogen or methyl;

$X_3$ is hydrogen or halogen; and

A is —Si($R_5$)($R_6$), wherein $R_5$ is $C_1$-$C_6$alkyl, $C_3$-$C_6$cycloalkyl, $C_1$-$C_6$alkoxy, phenyl, or phenyl substituted by halogen or methoxy;

$R_6$ is $C_1$-$C_6$alkyl or $C_1$-$C_6$alkoxy;

or alternatively $R_5$ and $R_6$ together represent a saturated 5- to 7-membered heterocycle having a maximum of 2 oxygen or sulfur atoms as additional hetero atoms.

2. A compound according to claim 1, wherein $R_5$ is $C_1$-$C_3$alkyl, $C_1$-$C_4$alkoxy, phenyl or fluorophenyl; and $R_6$ is $C_1$-$C_3$alkyl or $C_1$-$C_4$alkoxy.

3. A compound according to claim 1, wherein $R_5$ and $R_6$ together represent a saturated 5- or 6-membered heterocycle having a maximum of 2 oxygen atoms as additional hetero atoms and which heterocycle is unsubstituted or substituted by one or two methyl groups.

4. An agricultural composition which contains, as active ingredients, a microbicidially effective amount of at least one compound of formula I according to claim 1, together with customary carriers and adjuvants.

5. A composition according to claim 4, wherein the active ingredient is a compound according to claim 2.

6. A composition according to claim 4, wherein the active ingredient is a compound according to claim 3.

* * * * *